United States Patent [19]

Meilland

[11] Patent Number: Plant 5,622

[45] Date of Patent: Jan. 7, 1986

[54] ROSE PLANT-MEIJASON VARIETY

[75] Inventor: Marie L. Meilland, Antibes, France

[73] Assignee: The Conrad-Pyle Company, West Grove, Pa.

[21] Appl. No.: 592,429

[22] Filed: Mar. 21, 1984

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which particularly is suited for growing under glass to produce highly attractive cut flowers. The double blossoms exhibit an elegant appearance and are of a unique light cream yellow coloration which is lightly margined with luminous pink. The blossoms advantageously exhibit a very long vase life and the petals detach cleanly.

18 Drawing Figures

SUMMARY OF THE INVENTION

The object of the present invention is to provide a new variety of rose plant of the Hybrid Tea Class which can be distinguished from prior varieties by the following combination of characteristics:

(a) a strong and vigorous upright growth habit, (b) the ability to grow well under greenhouse conditions to produce cut flowers having a very long vase life which bear petals which detach cleanly, (c) forms attractive fully double blossoms of a light cream yellow coloration which are lightly margined with luminous pink, and (d) shows good resistance to fungus diseases.

Flowers having the coloration of the present variety are believed to be unique in a variety which is primarily devoted to the production of cut flowers under greenhouse conditions. Since the new variety is well adapted to forcing, it has the ability to fulfill well the needs of the cut flower industry. Also, its strong and vigorous growth rate is noteworthy.

The new variety was produced during the course of a controlled plant breeding program wherein the respective parents were chosen because of their possession of desired characteristics.

The female parent (seed parent) was the product of an artificial pollination of an unnamed variety and the JELFAX variety (non-patented) which in turn was crossed with the MEIGERIUM variety (U.S. Plant Pat. No. 3,803). The male parent (pollen parent) was an unnamed variety. The parentage of the new variety can be summarized as follows:

[(unnamed seedling × JELFAX) × MEIGERIUM] × unnamed seedling.

The seeds resulting from this pollination were sown and 120 distinct and different progeny arose. Selective study resulted in the identification of a single plant of the new variety. Extensive testing has confirmed the characteristics of the new variety.

The characteristics and properties of this new variety have been found to be transmissible by asexual propagation (i.e. winter bench grafting, dormant eye grafting, and grafting on various understocks). The results have conclusively established that the new vareity is easily reproduced asexually and that its characteristics are fully transmitted to the offspring through succeeding generations.

The rose plant of the new variety has been named the MEIJASON variety.

BRIEF DESCRIPTION OF THE PHOTOGRAPH

The accompanying photograph shows as nearly true as it is reasonably possible to make the same in color illustration of this character, typical specimens of plant parts from plant growing on Rosa indica understock in a greenhouse during September at Cap d'Antibes, France. Illustrated in:

FIG. 1 is a specimen of a young shoot;

DETAILED DESCRIPTION

Figures 2, 3, 4, 5, 6, 7, 8, 9, 10, 11, 12, 13, 14, 15, 16, 17, 18:
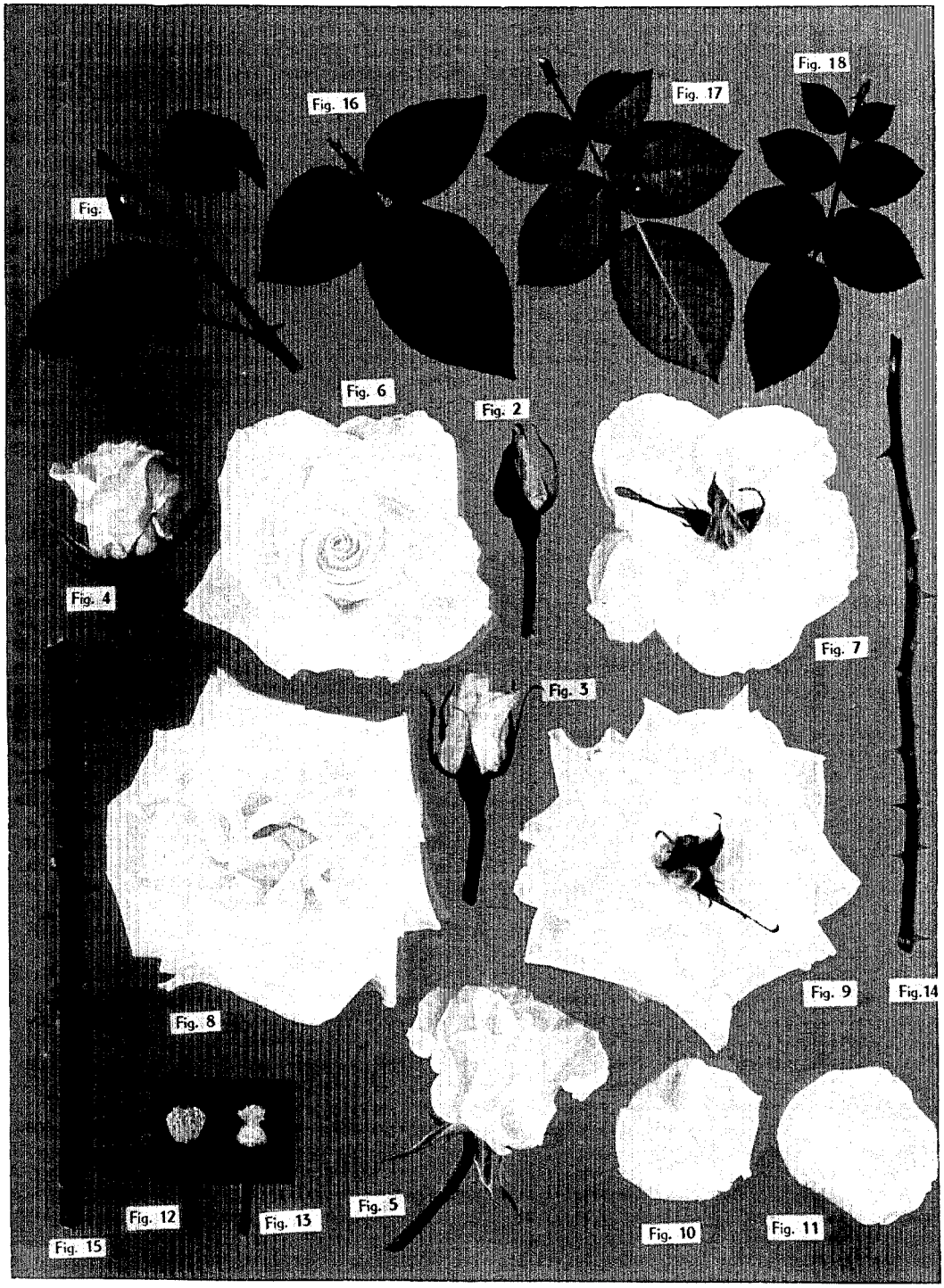
FIG. 2 is a specimen of a flower bud at the opening of the sepals.
FIG. 3 is a specimen of a flower bud at the opening of the petals.
FIG. 4 is a specimen of a flower as opening begins.
FIG. 5 is a specimen of a flower in the course of opening.
FIG. 6 is a specimen of a fully open flower — plan view — obverse.
FIG. 7 is a specimen of a fully open flower — plan view — reverse.
FIG. 8 is a specimen of a fully open flower just prior to petal drop — plan view — obverse.
FIG. 9 is a specimen of a fully open flower just prior to petal drop — plan view — reverse.
FIG. 10 is a specimen of a petal — obverse.
FIG. 11 is a specimen of a petal — reverse.
FIG. 12 is a specimen of a receptacle showing the arrangement of the stamens (sepals removed)
FIG. 13 is a specimen of a receptacle showing the arrangement of the pistils (sepals and stamens removed)
FIG. 14 is a specimen of a young flowering stem.
FIG. 15 is a specimen of a main branch.
FIG. 16 is a specimen of a leaf with 3 leaflets — upper surface.
FIG. 17 is a specimen of a leaf with 5 leaflets — under surface.
FIG. 18 is a specimen of a leaf with 7 leaflets — upper surface.

The rose plants of the new variety described were being grown in a greenhouse during September on *Rosa indica* understock at Cap d'Antibes, France.

The chart utilized in the identification of the colors is that of The Royal Horticultural Society (R.H.S. Colour Chart). In some instances terminology precedes the numbered references to this chart to designate in common terms the corresponding colors:

Class: Hybrid Tea.

Plant:

*Height.*—When plants are pruned to approximately 0.85 meter, floral stems of approximately 0.3 to 0.7 meter are obtained.

*Bearing.*—Upright.

Branches:

*Color.*—Young stems: Light green, Yellow-Green Group 146B. Mature wood: Dark green, Yellow-Green Group 147A.

*Thorns.*—Shape-upper edge: Straight and slightly inflected toward the base. Shape-lower edge: Concave. Size: Medium. Quantity: Numerous. Color on young stems: Reddish-green. Color on mature wood: Straw color.

Foliage:

*Stipules.*—Adnate, large and linear.

*Petiole.*—Upper surface: Reddish-brown on young foliage with sometimes a reddish tinge on the more adult foliage. Under surface: Light green, sometimes bears several small thorns.

*Leaflets.*—Number: 3,5 (most frequently) and 7. Shape: Elliptic, lancelate. Serrations: Simple and regular. General effect: Very ample and dense foliage having a somewhat dull appearance.

*Color.*—Young leaves: Upper surface: Light green, 146B Yellow-Green Group, more or less suffused with a reddish-brown tinge. Under surface: Reddish-brown and somewhat shaded with green. Adult leaves: Upper surface: Dark green, Yellow-Green Group 147A. Under surface: Medium green, Yellow-Green Group 147B.

Flowers:

*Number of flowers.*—Generally one flower per stem during greenhouse forcing; however, from time to time the buds at the top of the stem develop into flowering buds as well.

*Peduncle.*—Straight and rigid with numerous small thorns along its length, approximately 11 cm. in length on average.

*Sepals.*—Upper surface: Tomentose and greenish in coloration. Under surface: Medium green with somewhat glandular sides, external sepals tend to be straight and narrow.

*Bud.*—Shape: In the form of a conicle before the opening of the sepals. Length: Approximately 3 cm. on the average. Size: Medium. Color on opening: Upper surface: Yellow Group 6C and somewhat darker on the central petals. Under surface: Yellow Group 11B suffused with an azelea pink tone and Red Group 38A on the external petals.

*Flower.*—Shape: Sides are parallel, fully double. Diameter: Approximately 12 cm. on average. Color-when first opening: Inner surface: Pale yellow, Yellow Group 6D, darker toward the center of petals. Outer surface: Generally light yellow, Yellow Group 8B, suffused with azelea pink, Red Group 38B on external petals, internal petals are Yellow Group 6C. Color-during course of opening: inner surface: Cream Yellow, Yellow Group 4D, becoming somewhat darker on the interior petals, suffused with a pink tonation toward the margins with Red Group 49A. Outer surface: Yellow Group 4D, becoming slightly darker on the interior petals, lightly suffused toward the margins with Red Group 49A. Color when fully open: Inner surface: Yellow Group 4D, fading somewhat on the external petals, suffused somewhat with Red Group 49A on the petal margins. Outer surface: Yellow Group 4D, fading somewhat at the center on the external petals, slightly suffused with Red Group 43D on petal margins. Fragrance: Slight. Lasting quality in vase: Very long. Stamens: Approximately 104 on average, anthers are straw colored with fuschsia margins. Pistils: Approximately 96 on average, stigmas are yellow and slightly tinged with ochre.

Development:

*Vegetation.*—Vigorous.

*Flowering.*—Abundant.

*Aptitude to forcing.*—Very good.

*Resistance to diseases.*—Excellent.

I claim:

1. A new and distinct variety of Hybrid Tea rose plant, substantially as illustrated and described, which is capable of exhibiting the following combination of characteristics:

(a) a strong and vigorous upright growth habit, (b) the ability to grow well under greenhouse conditions to produce cut flowers having a very long vase life which bear petals which detach cleanly, (c) forms attractive fully double blossoms of a light cream yellow coloration which are lightly margined with luminous pink, and (d) shows good resistance to fungus diseases.

* * * * *

Fig.